US 6,528,812 B1

(12) United States Patent
Leblans et al.

(10) Patent No.: US 6,528,812 B1
(45) Date of Patent: Mar. 4, 2003

(54) RADIATION IMAGE READ-OUT METHOD AND APPARATUS

(75) Inventors: Paul Leblans, Kontich (BE); Luc Struye, Mortsel (BE)

(73) Assignee: Agfa-Gevaert, Mortsel (BE)

( * ) Notice: Subject to any disclaimer, the term of this patent is extended or adjusted under 35 U.S.C. 154(b) by 0 days.

(21) Appl. No.: 09/596,519

(22) Filed: Jun. 19, 2000

Related U.S. Application Data

(60) Provisional application No. 60/142,276, filed on Jul. 2, 1999, and provisional application No. 60/159,004, filed on Oct. 8, 1999.

(51) Int. Cl.$^7$ .............................................. G03B 42/08
(52) U.S. Cl. ..................... 250/588; 250/581; 250/584
(58) Field of Search .......................... 250/484.2, 484.3, 250/484.4, 588, 581, 582, 583, 584, 585, 589

(56) References Cited

U.S. PATENT DOCUMENTS 3,859,527 A    1/1975   Luckey
4,835,386 A  * 5/1989   Shimura et al. ......... 250/327.2
5,028,509 A    7/1991   Shimada et al.
5,076,963 A  * 12/1991  Kameyama et al. ... 252/301.36
5,657,335 A  * 8/1997   Rubin et al. .................. 372/44
5,804,832 A  * 9/1998   Crowell et al. ............. 250/580
5,864,146 A  * 1/1999   Karellas ...................... 250/581
5,877,508 A  * 3/1999   Arakawa et al. ............ 250/588

FOREIGN PATENT DOCUMENTS

EP          0 174 875       6/1990

* cited by examiner

Primary Examiner—Constantine Hannaher
Assistant Examiner—Tim Moran
(74) Attorney, Agent, or Firm—John A. Merecki; Hoffman, Warnick & D'Alessandro

(57) ABSTRACT

A radiation image that has been stored in photostimulable phosphor screen comprising a divalent europium activated cesium halide is read out by stimulating the phosphor screen by means of stimulating radiation, detecting light emitted by the phosphor screen upon stimulation and converting the detected light into a signal representation of said radiation image. After read out the phosphor screen is erased by exposing it to erasing light emitted by at least one electroluminescent lamp or by an array of light emitting diodes.

12 Claims, 3 Drawing Sheets

RADIATION IMAGE READ-OUT METHOD AND APPARATUS

This is a continuation-in-part of copending U.S. Appln. No. 60/142,276 filed Jul. 2, 1999 and Appln. No. 60/159,004 filed Oct. 8. 1999.

FIELD OF THE INVENTION

The present invention relates to a method and a system of reading a radiation image that has been stored in a photostimulable phosphor screen, wherein the photostimulable phosphor screen can be re-used. The invention further relates to a re-usable radiation detector.

BACKGROUND OF THE INVENTION

Radiation image recording systems wherein a radiation image is recorded on a photostimulable phosphor screen by exposing said screen to image-wise modulated penetrating radiation are widely used nowadays.

The recorded image is reproduced by stimulating the exposed photostimulable phosphor screen by means of stimulating radiation and by detecting the light that is emitted by the phosphor screen upon stimulation and converting the detected light into an electrical signal representation of the radiation image.

In such a system it is preferred, in view of economy, that the stimulable phosphor screen can be used in many imaging cycles.

The reuse of the stimulable phosphor screen is possible when the previously stored radiation image is erased to a sufficient extent.

When reading out an image by scanning a phosphor screen that has been exposed to penetrating radiation, less than 90% of the stored energy is released. Thus there arises a problem that, upon reuse, part of the radiation image is still stored in the phosphor screen and can appear in the subsequent image as a so-called ghost image.

In general medical radiography, images are made with widely differing X-ray doses.

To make images of extremities, like e.g. fingers, doses are used of the order of 1 mR. On the other hand, images of internal organs, like the stomach are made with X-ray doses that may be as high as 300 mR.

To avoid ghosting, when making a 1 mR image immediately after a 300 mR image, the signal of the first image must be reduced by more than a factor of 300.

As a matter of fact, a dynamic range is desired in the second image of at least 100. This implies that the signal created by the first irradiation must be reduced by a factor of at least $3.10^4$, which is equivalent to requiring an erasure depth of $1/(3.10^4) = 3.3.10^{-5}$.

According to U.S. Pat. No. 3,859,527 (column 4, lines 5–7) the phosphor can be reduced to neutral state by actions like a uniform illumination, irradiation or heating.

In commercial systems, the phosphor screen is erased by illumination with visible light.

Commonly incandescent lamps are used because they are cheap, high power light sources. High power light sources are selected, because in order to guarantee a high throughput scanning system, the phosphor screen must be erased in a short time. High power lamps, however, generate a lot of heat, which may destabilise the scanner to read out the storage phosphor screens. In order to sufficiently remove the heat generated by the high power lamps the size of the erasing unit has to be rather large.

Furthermore, in case incandescent lamps are used in an erasure unit of a phosphor read out apparatus, the dimensions of the phosphor erasure unit are determined by the dimensions (more specifically the diameter) of the incandescent lamps.

OBJECTS OF THE INVENTION

It is an object of the present invention to provide a method and a system for reading a radiation image on a photostimulable phosphor screen wherein the screen is erased in between successive recordings to an adequate extent so as to permit re-use of the screen.

It is a further object of the present invention to provide such a system that is compact and has at the same time a high throughput.

Still another object is to provide a compact re-usable radiation detector.

Further objects will bercome apparent from the description given below.

SUMMARY OF THE INVENTION

The inventors have found that the above mentioned objects are realised by a method of reading a radiation image that has been stored in a photostimulable phosphor screen comprising the steps of (1) stimulating said phosphor screen by means of stimulating radiation, (2) detecting light emitted by the phosphor screen upon stimulation and converting the detected light into a signal representation of said radiation image, (3) erasing said phosphor screen by exposing it to erasing light, wherein (4) said phosphor is a divalent europium activated cesium halide phosphor wherein said halide is at least one of chloride and bromide, and (5) said erasing light is emitted by at least one electroluminescent lamp.

In this document the term "radiation" has to be understood as any penetrating radiation and includes irradiation originating from a radioisotope (e.g. Co60, Ir192, Se75, etc.), radiation created by an X-ray generator of any type, radiation and high energy particles created by a high energy radiation generator (e.g. Betatron), radiation from a sample labelled with a radioisotope as is the case in e.g. autoradiography.

An electroluminescent lamp can be in the form of an electroluminescent film based on an inorganic electroluminescent phosphor, e.g. ZnS:Mn, or an electroluminescent film based on organic light-emitting diodes (OELDs).

The use of electroluminescent lamps in the present invention is advantageous in that these lamps are ideal for uniform illumination applications.

While eliminating the need for sockets, bulbs, diffusers and reflectors, these lamps provide uniform lighting across the entire lamp surface. The lamps are a cold light source, so little heat is added to the assembly.

Most light emitting devices vary in luminance according to the direction. Electroluminescent lamps have essentially the same luminance independent of angle, i.e. an electroluminescent lamp is a Lambertian emitter.

Moreover, electroluminesent lamps can be made with an emitting surface that is of the same size as the surface of the phosphor screen that must be erased. This makes it possible to erase phosphor screens in a very homogeneous way.

Nevertheless a prejudice exists against the use of electroluminescent lamps as erasing light source in a photostimulable phosphor read out system because the power of the light source is low and consequentially these lamps are thought to be inadequate for obtaining a sufficient erasure depth so as to enable re-use of the photostimulable phosphor screen.

The inventors have found that by using a specific phosphor, more specifically a divalent europium activated caesium halide phosphor, wherein said halide is at least one of chloride and bromide, erasure to a sufficient extent can be obtained with a low power and compact electroluminescent lamp. In this way the erasure device can be made very compact without implying a longer erasure time and consequentially a lower throughput.

Another aspect of the present invention relates to a radiation image read out apparatus as set out in claims 8 to 12.

The compactness of an erasure unit which comprises an electroluminescent lamp makes it appropriate for integration in a radiation detector according to the present invention.

Still another aspect thus relates to a radiation detector as set out in claim 13 and following claims.

Specific features for preferred embodiments of the invention are disclosed in the dependent claims.

In a first embodiment of the method, of the system and of the detector according to the present invention (an) electroluminescent lamp(s) is(are) used that is(are) based on inorganic electroluminescent phosphors as e.g. ZnS:Mn, ZnS:Cu, CaS:Eu, CaS:Ce.

These electroluminescent lamps can have an optical power of upto ca. 0.3 $mW/cm^2$.

Furthermore, by adjusting the phosphor composition and the operating frequency of the lamp, the light spectrum emitted by the electroluminescent lamp can be matched with the erasure spectrum of the phosphor. Hence, electroluminescent lamps lead to higher erasure depth as incandescent lamps at equal optical power while having much smaller dimensions and dissipating less heat.

It will further be explained that an optical energy of 10 $mJ/cm^2$ is needed to erase a $CsBr:Eu^{2+}$ phosphor to a sufficient extent. This implies that the $CsBr:Eu^{2+}$ phosphor can be erased with an electroluminescent lamp in about 35 s.

When compared with the energy needed to erase a commercially available $BaFBr:Eu^{2+}$ phosphor screen, denoted by the trade name MD-10 of Agfa-Gevaert N.V., at least 100 times more energy would be needed for erasure. This would corresponds to an erasure time of ca. 1 hour. An erasure process of this duration would be unacceptable for commercial purposes.

The use of an electroluminescent lamp in combination with a $CsBr:Eu^{2+}$ phosphor is furthermore advantageous in that this combination provides very homogeneous erasure in a compact erasure unit.

When compared with a situation wherein a $BaFBr:Eu^{2+}$ phosphor would have been used, a similar result could only be obtained with very long erasure times, which is highly impractical.

Erasure of the $CsBr:Eu^{2+}$ phosphor screen can take place in a compact erasure unit in the digitiser. The electroluminescent lamps being very flat, however, erasure can also take place in the cassette, or in a box, in which the storage phosphor screens are stored. In this way a re-usable radiation detector can be made.

In a second embodiment an organic electroluminescent lamp (OELD) is used. Although this type of electroluminescent lamps is more expensive, it is even more suited for use in a storage phosphor erasure unit because this type of lamps allows even shorter erasure times as will be explained below.

Organic electroluminescent devices are either based on vacuum-evaporated small organic molecules or on polymers. The former class of organic electroluminescent lamps are usually called OELD, the latter Polymer ELD.

The most simple organic electroluminescent lamp structure consists of a single layer between two suitable contacts: for the hole-injection anode ITO (Indium Tin Oxide) is frequently used while for the electron-injection cathode a Mg—Ag alloy, Al or Ca is used.

The operation is as follows: in organic electroluminescent lamps electrons and holes are injected into a rather well insulating layer, where they recombine via a process that leads to the emission of a photon.

The organic electroluminescent lamp has a very thin layer (about 100 nm) and the voltage is low (<10V).

For a voltage of ca. 10 V, organic electroluminescent devices reach an efficiency of ca. 2 $mW/cm^2$. This means that the optical power of these devices is an order of magnitude higher than the optical power of inorganic electroluminescent lamps. With organic electroluminescent devices the erasure time can therefore be reduced by an order of magnitude, which brings the erasure time down to ca. 5 s. This duration is adapted for use in actual commercial scanners for storage phosphor screens.

Another aspect of this invention relates to the use of light emitting diodes (LED) as erasing light source(s) in a photostimulable phosphor read out method, system and detector as set out in claims 4, 9 and 14.

Arrays of light emitting diodes are almost equally compact as electroluminescent lamps, in addition they have a higher optical power. This implies that they are very suitable for the construction of a compact erasure unit that will erase the phosphor plate very homogeneously.

By using a specific phosphor, more specifically a divalent europium activated cesium halide phosphor, wherein said halide is at least one of chloride and bromide, erasure to a sufficient extent can be obtained with a low power and compact light emitting diodes within a short period of time. In this way the erasure unit can be made very compact without implying a longer erasure time and consequentially a lower throughput.

Light emitting diodes with a size of 3 mm×3 mm may have a luminance of upto 500 mCd. Arrays of such light emitting diodes will have an optical power of 5 $Cd/m^2$. This corresponds to ca. 50 $mW/cm^2$.

An erasure unit, made up of an LED array with an emitting area of ca. 60 $cm^2$ can be used, therefore, in order to erase a $CsBr:Eu^{2+}$ in 5 s. Alternatively an LED array with an emitting area of 300 $cm^2$ can be used to erase a $CsBr:Eu^{2+}$ screen of 43 cm×35 cm in 1 s.

The present invention as well as specific and/or preferred embodiments hereof will be explained in the detailed description given below. Particular aspects will be illustrated by the drawings enumerated hereinafter.

DETAILED DESCRIPTION OF THE INVENTION

Figure 1:
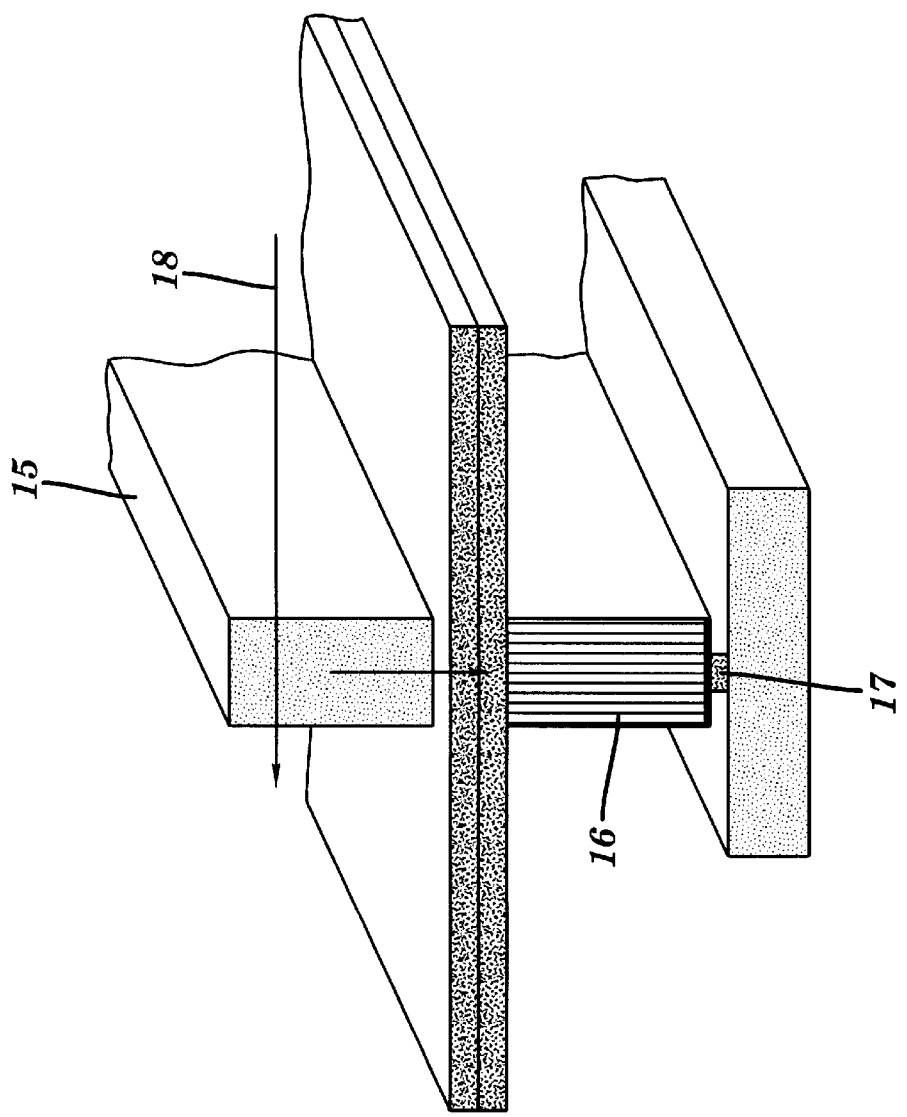
FIG. 1 shows a first embodiment of photostimulable phosphor read out apparatus, referred to as scan-head type, FIG. 2 schematically shows the position of the stimulating light source and the erasing light source in the embodiment of FIG. 1.

An embodiment of a read out apparatus according to the present invention is shown in FIG. 1. This embodiment is referred to as the scan-head type.

The read out unit comprises a linear light source (15) for emitting stimulating light onto the photostimulable phosphor screen.

This linear light source comprises e.g. 10 to 20 individual laser diodes arranged in a row, the light which is emitted being projected onto the screen through a cylindrical lens.

The read out unit further comprises a fiber optic plate (16) for directing light emitted by the phosphor screen upon stimulation onto a linear array of sensor elements (17), more particularly charge coupled devices. The fiber optic plate (16) comprises a number of parallel mounted light guiding fibers arranged so as to guide the light emitted by each individual element of an illuminated line onto a sensor element.

Alternatively the fiber optic plate can be replaced by an arrangement of selfoc lenses or microlenses.

Alternatives may also be envisaged for the linear light source. This linear light source can be replaced by a 'flying spot' light source. The light emitted by this light source is then deflected e.g. by a rotatable polygon mirror onto a scan line on the phosphor screen. In this way one point of this line at the time is illuminated.

Figure 3:
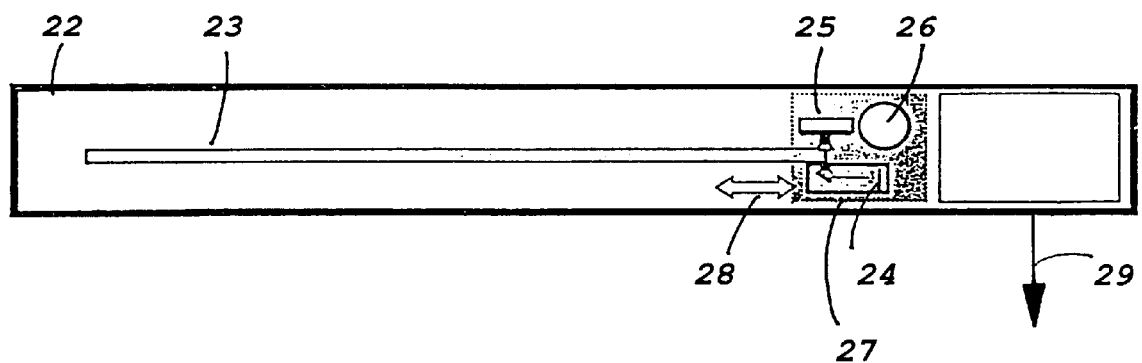
FIG. 3 shows an embodiment of a radiation detector according to the present invention.

In the embodiment shown in FIG. 3 the linear light source is arranged on one side of the phosphor screen, the fiber optic plate and the linear array of sensor elements being arranged on the opposite side. Either of these elements extends in the direction of a scan line.

During read out, the phosphor screen on the one hand and the assembly of fiber optic plate and sensor array on the other hand are displaced relative to each other in the direction of arrow (18).

In still another embodiment which is not shown the array of stimulating light sources, the fiber optic plate and the sensor array are arranged at the same side of the photostimulable phosphor screen.

After read out the photostimulable phosphor screen is erased so that the energy remaining in the screen after read out is released and so that the screen is in a condition for re-use.

In the type of read out apparatus wherein stimulation is performed by means of light emitted by a linear light source extending parallel to a scan line on the stimulable phosphor screen, the erasure unit preferably forms part of the read out unit.

Figure 2:
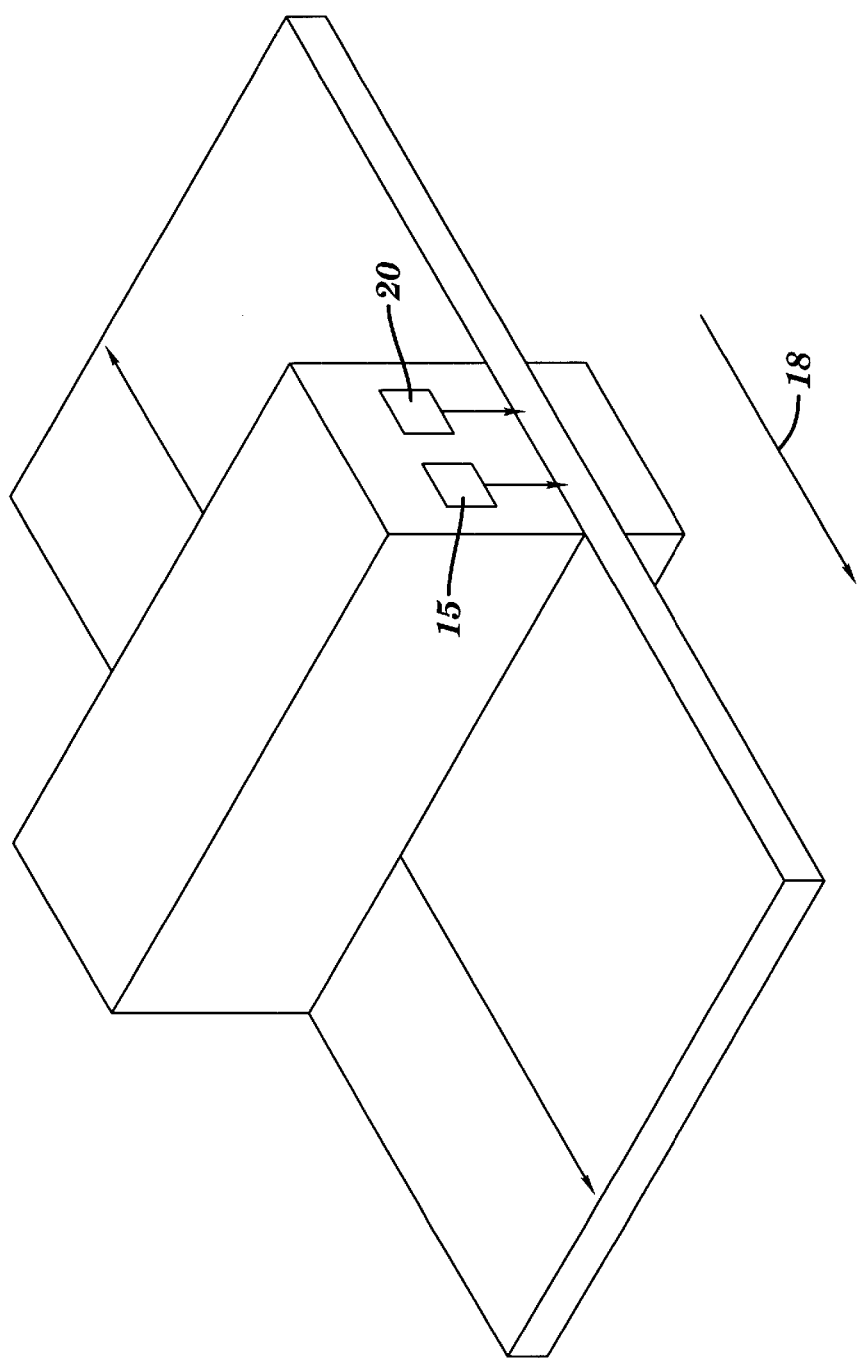

In the embodiment shown in FIG. 1, the erasing light source (20) is part of an assembly comprising the stimulating light source and the light guiding and light detecting means. The position of the stimulating light source and of the erasing light source is shown schematically in FIG. 2.

In one embodiment according to the present invention the erasing section comprises a rectangular array of LEDs with an emitting area of between 15 and 300 cm$^2$ emitting light in the wavelength range of 600 to 750 nm. The required area depends on the desired erasure time: the larger the area, the shorter will be the required erasure time. The number of LEDs in the array depends in the size of the LEDs and is typically in the order of 50 to 2000.

The array of light emitting diodes is arranged parallel to the linear array of stimulating light sources. The erasing light source and the array of source s of stimulating light are transported past the image that is read at the same transportation speed in between 30 mm/sec and 250 mm/sec. In this way the erasing light source illuminates a line of the image after it has been subjected to read out.

In an alternative embodiment according to the present invention the erasure unit comprises an electroluminescent lamp. As has been described higher, this type of lamp constitutes a flat light emitting surface. Such a surface or area can be provided in a separate erasing unit through which the phosphor screen is transported after having been read out so that the screen is subjected to erasing light emitted by the electroluminescent lamp.

However, alternative embodiments may be envisaged. The electroluminescent lamp may for example be part of the read out assembly itself. It may for example be part of the cover of the apparatus. In such an embodiment the electroluminescent lamp is activated once read out is finished.

Another aspect of the present invention relates to a re-usable radiation detector. This type of detector is shown in FIG. 3.

The detector comprises an enclosure (22).

Within the enclosure a photostimulable phosphor screen (23) is positioned. This screen preferably comprises a divalent cesium halide phosphor, wherein said halide is at least one of chloride and bromide. This phosphor has very good erasability characteristics and additionally provides optimal sharpness.

The enclosure further comprises at least one source of stimulating light (24) arranged for stimulating said phosphor screen and an array of transducer elements (25) capturing light emitted by the phosphor upon stimulation and for converting said light into an electrical signal representation. In the embodiment that is illustrated a linear array of stimulating light sources is used, more specifically an array of laser diodes. The illustrated embodiment further comprises a linear array of transducer elements more specifically charge coupled devices.

The enclosure further comprises an erasing light source.

In one embodiment the erasing light source is a linear erasing light source (26), more specifically an array of 50 to 2000 individual light emitting diodes emitting light in the wavelength range of 600 to 750 nm and covering an emitting area of 15 to 300 cm$^2$. The array is arranged substantially parallel to the stimulating light source.

In another embodiment the erasing light source is an electroluminescent lamp which is arranged so as to be able to illuminate the entire phosphor screen area when it is activated. The lamp is activated once the read out of the screen is terminated.

This type of lamp can for example be provided on the inner surface of the part of enclosure (22) which faces the photostimulable phosphor screen. Such an embodiment can be made very compact.

Alternatives, such as the provision of a separate erasing unit which is positioned adjacent to the readout unit so that the screen is transported from the read out unit to the erasing unit are possible.

The enclosure further comprises means (not shown) for transporting the assembly (27) of stimulating light source and array of transducer elements and occasionally the erasing light source relative to the phosphor screen in a so-called sub-scan direction, indicated by arrow (28).

Means (29) are further provided for communicating the electrical signal representation output by the array of transducer elements to an external signal processing device.

In this embodiment the stimulating light source and the array of transducer elements are arranged on opposite sides of the phosphor screen.

In alternative embodiments these items may be arranged on the same side of the phosphor screen.

The stimulable phosphor screen in the several embodiments of the present invention comprises a divalent europium activated cesium halide phosphor. Such a phosphor is known in the art and has for example been disclosed in EP-A-174 875 (and U.S. Pat. No. 5,028,509). The phosphor is especially well suited for manufacturing 'binderless' phosphor screens. Binderless phosphor screens provide optimal sharpness. They further have very good erasability as will be shown furtheron.

It is advantageous to use a CsX:Eu phosphor wherein X represents a halide selected from the group consisting of Br and Cl, which is obtained by the following method:

mixing CsX with between $10^{-3}$ and 5 mol % of a Europium compound selected from the group consisting of $EuX'_2$, $EuX'_3$ and EuOX', X' being a member selected from the group consisting of F, Cl, Br and I, firing the mixture at a temperature above 450° C.

cooling said mixture and recovering the CsX:Eu phosphor.

A phosphor that has been obtained as a result of the above method of preparation has an increased conversion efficiency compared to the state of the art divalent europium activated cesium halide phosphor. The phosphor can be stimulated by means of a lower amount of stimulation energy.

A photostimulable phosphor screen using such a phosphor is preferably obtained by the method of preparing said CsX:Eu phosphor by firing a mixture of said CsX with between 10-3 and 5 mol % of an Europium compound selected from the group consisting of $EuX'_2$, $EuX'_3$ and EuOX', X' being a halide selected from the group consisting of F, Cl, Br and I and applying said phosphor on a substrate by a method selected from the group consisting of physical vapour deposition, thermal vapour deposition, chemical vapour deposition, radio frequency deposition and pulsed laser deposition.

This method of preparation is advantageous because it allows to deposit the phosphor in the form of needle-shaped crystals. These needle-shaped phosphor crystals act as light guides so that they reduce the lateral spreading of light in the phosphor layer. Reduced lateral light spread leads to images of higher resolution.

Alternatively a phosphor screen containing a CsX:Eu stimulable phosphor, wherein X represents a halide selected from the group consisting of Br and Cl can also be manufactured by performing the steps of:

bringing multiple containers of said CsX and an Europium compound selected from the group consisting of $EuX'_2$, $EuX'_3$ and EuOX', X' being a halide selected from the group consisting of F, Cl, Br and I in condition for vapour deposition and depositing, by a method selected from the group consisting of physical vapour deposition, thermal vapour deposition, chemical vapour deposition, electron beam deposition, radio frequency deposition and pulsed laser deposition, both said CsX and said Europium compound on a substrate in such a ratio that on said substrate a CsX phosphor, doped with between $10^{-3}$ and 5 mol % of an Europium compound, is formed.

This method is advantageous because it allows to deposit the phosphor in the form of needle-shaped crystals. These needle-shaped phosphor crystals act as light guides so that they reduce the lateral spreading of light in the phosphor layer. Reduced lateral light spread leads to images of higher resolution.

The above-described specific phosphors as well as their methods of preparation have been disclosed in U.S. provisional applications Nos. 60/159,004 and 60/142,276 which are incorporated herein-by reference.

Measurements of Erasibility

The erasability of a CsBr:Eu screen was measured in comparison to a commercial MD-10 (trade name of Agfa-Gevaert N.V.) BaFBr:Eu screen of Agfa-Gevaert N.V.

Sample Preparation

The CsBr:Eu screen was produced in the following way:

A CsBr:Eu sample screen was made via thermal vapour deposition of CsBr and the EuOBr. To this aim, CsBr was mixed with EuOBr and placed in a container in a vacuum deposition chamber. The phosphor was deposited on a glass disk with a thickness of 1.5 mm and a diameter of 40 mm. The distance between the container and the substrate was 10 cm. During evaporation, the substrate was rotated at 12 rpm.

The substrate temperature was ca. 200° C. at the start of the evaporation process.

The container was heated to a temperature of 750° C.

Before the start of the evaporation, the chamber was evacuated to a pressure of $4.10^{-5}$ mbar. During the evaporation process, Ar was introduced in the chamber and the Ar gas pressure was $1.6\ 10^{-2}$ mbar.

The resulting screen had a thickness of 850 m.

The Eu-concentration in the evaporated screen was measured with X-ray fluorescence. At the substrate side, the phosphor contained 400 ppm of Eu and at the surface side 800 ppm.

Measurement Procedure

In a first measurement, both screens were homogeneously irradiated with a dose of ca. 50 mR at 80 kVp.

The screens were read out in a flying spot scanner. The scanning light source was a 30 mW diode laser emitting at 690 nm. A 4 mm Hoya BG-39 (trade name) filter was used to separate the stimulation light from the light emitted by the phosphor screen. The scan-average levels (SAL) were determined as the average signal produced by the screens in the photomultiplier tube. The results of this measurement was a SAL1 value for the CsBr:$Eu^{2+}$ screen and a SAL1 value for the MD-10 screen (Table 1).

In a second measurement, the MD-10 screen was homogeneously irradiated with a dose of ca. 44 R, also at 80 kVp.

Next, the screen was erased with a 500 W (electrical power) quartz-halogen lamp for 1 s. The light intensity at the screen position was measured using a photometer and was 12 mW/cm$^2$.

After erasure, the screen was read out with the above-described scanner, and the SAL was measured. This measurement yielded the SAL2 value for the MD-10 screen (Table 1).

Erasure depth, defined as the SAL after erasure divided by the SAL prior to erasure was calculated using the equation:

$$Ed = SAL2 \times 50/(SAL1 \times 44{,}000) \qquad (1),$$

where the factor 50/44,000 corrects for the difference in dose in the measurements 1 and 2. (Different doses were selected in order to enable image detection in all cases without having to adapt the sensitivity settings of the photomultiplier).

In a third measurement, the CsBr:$Eu^{2+}$ screen was homogeneously irradiated with a dose of ca. 166 R, also at 80 kVp.

Next, the screen was erased with the 500 Watt quartz-halogen lamp for 1 s. The light intensity on the screen was, again, 12 mW/cm$^2$.

After erasure, the screen was read out with the above-described scanner, and the SAL was determined. This measurement yielded the Erasure depth, defined as the SAL after erasure divided by the SAL prior to erasure was calculated using the equation:

$$E_d = SAL3 \times 50/(SAL1 \times 166,000) \quad (2),$$

where the factor 50/166,000 corrects for the difference in dose in the measurements 1 and 3.

TABLE 1

Measured SAL values and calculated Ed values for MD-10 and CsBr:Eu$^{2+}$ screens

|  | MD-10 BaFBr:Eu$^{2+}$ | CsBr:Eu$^{2+}$ |
| --- | --- | --- |
| SAL1 | 440 | 1,180 |
| SAL2 | 2,800 |  |
| SAL3 |  | 290 |
| Ed | 7.10-3 | 7.10-5 |

It is clear that CsBr:Eu has a much better erasability than the commercial BaFBr:Eu$^{2+}$ phosphor. As a consequence, much less erasure power is needed to erase the CsBr:Eu$^{2+}$ storage phosphor screen.

Hence, the object of the present invention can be accomplished by making an imaging system based on CsBr:Eu instead of BaFBr:Eu.

In a fourth set of measurements, the CsBr:Eu$^{2+}$ screen was erased with a monochromatic light source, as is more representative for erasure with an electroluminescent lamp.

For this purpose, a laser emitting at 685 nm was used and its beam was expanded to give an intensity of 0.125 mW/cm$^2$ on the screen to be erased.

In a first measurement the screen was homogeneously irradiated with a dose of 48 mR at 80 kVp.

The screen was read out with the above-described scanner, and the SAL was measured. This measurement yielded the SAL$_{41}$ value for the CsBr:Eu screen (Table 2).

Next, the CsBr:Eu screen was homogeneously irradiated with a doses ranging from 167 mR to 115 R and erased with the laser set-up for 1 to 100 s (Table 2).

After erasure, the screen was read out with the above-described scanner, and the SAL was measured. The measurements yielded the SAL$_{42}$ to SAL$_{48}$ values given in Table 2.

Erasure depth, defined as the SAL after erasure divided by the SAL prior to erasure was calculated using the equation:

$$E_d = SAL_{4x} 50/(SAL_{41} \times Dose(x)) \quad (2),$$

where the factor 50/Dose(x) corrects for the difference in measurements.

TABLE 2

Measured SAL values and calculated E$_d$ value for the CsBr:Eu$^{2+}$ screen for monochromatic erasure at 685 nm

| Measurement | X-ray dose (mR) | Erasure time (s) | SAL (V) | E$_d$ |
| --- | --- | --- | --- | --- |
| 41 | 48 | 0 | 917 | 1 |
| 42 | 167 | 1 | 842 | 2.6 10$^{-1}$ |
| 43 | 167 | 2 | 399 | 1.3 10$^{-1}$ |
| 44 | 234 | 5 | 142.5 | 3.2 10$^{-2}$ |
| 45 | 1,026 | 10 | 95.6 | 4.9 10$^{-3}$ |
| 46 | 25,400 | 20 | 323 | 6.6 10$^{-4}$ |
| 47 | 50,500 | 50 | 53.4 | 5.5 10$^{-5}$ |
| 48 | 115,000 | 100 | 17 | 7.7 10$^{-6}$ |

The results in Table 2 demonstrate that an erasure time of ca. 80 s is required in the used set-up to reach the desired erasure the depth of 3.10$^{-5}$.

With an erasure intensity of 0.125 mW/cm$^2$, this corresponds to a required erasure power of 10 mW/cm$^2$.

In other words, if a monochromatic erasure source, or an erasure source with a relatively narrow emission spectrum is used to erase the CsBr:Eu screen and if the erasure wavelength is in the region of the stimulation spectrum of CsBr:Eu, which extends from 600 to 700 nm, an optical power of ca. 10 mW/cm$^2$ is needed to reach the desired erasure depth of 3.10$^{-5}$.

What is claimed is:

1. A re-usable radiation detector comprising
   a photostimulable phosphor screen,
   at least one source of stimulating light arranged for stimulating said phosphor screen,
   an array of transducer elements arranged for capturing light emitted by the phosphor screen upon stimulation and for converting said light into an electrical signal representation,
   an erasing unit comprising an electroluminescent lamp arranged so as to illuminate said phosphor screen when being energised,
   means for transporting an assembly comprising the at least one stimulating light source, the erasing unit, and the array of transducer elements relative to the phosphor screen,
   an enclosure enclosing said photostimulable phosphor screen, the assembly comprising the at least one stimulating light source, the erasing unit, and the array of transducer elements, and the means for transporting said assembly,
   interfacing means for communicating said electrical signal representation to an external signal processing device.

2. A re-usable radiation detector according to claim 1 wherein said electroluminescent lamp is based on an inorganic electroluminescent phosphor.

3. A re-usable radiation detector according to claim 1 wherein said electroluminescent lamp is based on organic electroluminescent materials.

4. A re-usable radiation detector according to claim 1 wherein said phosphor screen comprises a divalent europium activated cesium halide phosphor wherein said halide is at least one of chloride and bromide.

5. A re-usable radiation detector according to claim 1 wherein said phosphor screen comprises a divalent europium activated cesium halide phosphor wherein said halide is at least one of chloride and bromide, said phosphor being obtained by the following steps:
   mixing CsX with between 10$^{-3}$ and 5 mol % of a europium compound selected from the group consisting of EuX'$_2$, EuX'$_3$ and EuOX', X' being a member selected from the group consisting of F, Cl, Br and I,
   firing the mixture at a temperature above 450° C.,
   cooling said mixture, and
   recovering the CsX:Eu phosphor.

6. A re-usable radiation detector according to claim 1 wherein said phosphor screen is obtained by the steps of
   preparing said CsX:Eu phosphor by firing a mixture of said CsX with between 10$^{-3}$ and 5 mol % of an europium compound selected from the group consisting of EuX'$_2$, EuX'$_3$ and EuOX', X' being a halide selected from the group consisting of F, Cl, Br and I, and
   applying said phosphor on a substrate by a method selected from the group consisting of physical vapour deposition, thermal vapour deposition, chemical vapour deposition, radio frequency deposition and pulsed laser deposition.

7. A re-usable radiation detector according to claim 1 wherein said phosphor screen is obtained by the steps of
   bringing multiple containers of said CsX and an europium compound selected from the group consisting of $EuX'_2$, $EuX'_3$ and $EuOX'$, X' being a halide selected from the group consisting of F, Cl, Br and I in condition for vapour deposition and
   depositing, by a method selected from the group consisting of physical vapour deposition, thermal vapour deposition, chemical vapour deposition, electron beam deposition, radio frequency deposition and pulsed laser deposition, both said CsX and said europium compound on a substrate in such a ratio that on said substrate a CsX phosphor, doped with between $10^{-3}$ and 5 mol % of an europium compound, is formed.

8. A re-usable radiation detector comprising
   a photostimulable phosphor screen,
   at least one source of stimulating light arranged for stimulating said phosphor screen,
   an array of transducer elements arranged for capturing light emitted by the phosphor screen upon stimulation and for converting said light into an electrical signal representation,
   an erasing unit comprising at least one array of light emitting diodes arranged so as to illuminate said phosphor screen when being energised,
   means for transporting an assembly comprising the at least one stimulating light source, the erasing unit and the array of transducer elements relative to the phosphor screen,
   an enclosure enclosing said photostimulable phosphor screen, the assembly comprising the at least one stimulating light source, the erasing unit, and the array of transducer elements, and the means for transporting said assembly,
   interfacing means for communicating said electrical signal representation to an external signal processing device.

9. A re-usable radiation detector according to claim 8 wherein said phosphor screen comprises a divalent europium activated cesium halide phosphor wherein said halide is at least one of chloride and bromide.

10. A re-usable radiation detector according to claim 8 wherein said phosphor screen comprises a divalent europium activated cesium halide phosphor wherein said halide is at least one of chloride and bromide, said phosphor being obtained by the following steps:
    mixing CsX with between $10^{-3}$ and 5 mol % of a europium compound selected from the group consisting of $EuX'_2$, $EuX'_3$ and $EuOX'$, X' being a member selected from the group consisting of F, Cl, Br and I,
    firing the mixture at a temperature above 450° C.,
    cooling said mixture, and
    recovering the CsX:Eu phosphor.

11. A re-usable radiation detector according to claim 8 wherein said phosphor screen is obtained by the steps of
    preparing said CsX:Eu phosphor by firing a mixture of said CsX with between $10^{-3}$ and 5 mol % of an europium compound selected from the group consisting of $EuX'_2$, $EuX'_3$ and $EuOX'$, X' being a halide selected from the group consisting of F, Cl, Br and I and
    applying said phosphor on a substrate by a method selected from the group consisting of physical vapour deposition, thermal vapour deposition, chemical vapour deposition, radio frequency deposition and pulsed laser deposition.

12. A re-usable radiation detector according to claim 8 wherein said phosphor screen is obtained by the steps of
    bringing multiple containers of said CsX and an europium compound selected from the group consisting of $EuX'_2$, $EuX'_3$ and $EuOX'$, X' being a halide selected from the group consisting of F, Cl, Br and I in condition for vapour deposition, and
    depositing, by a method selected from the group consisting of physical vapour deposition, thermal vapour deposition, chemical vapour deposition, electron beam deposition, radio frequency deposition and pulsed laser deposition, both said CsX and said europium compound on a substrate in such a ratio that on said substrate a CsX phosphor, doped with between $10^{-3}$ and 5 mol % of an europium compound, is formed.

* * * * *